US00PP16962P2

(12) United States Plant Patent
Verwer

(10) Patent No.: US PP16,962 P2
(45) Date of Patent: Aug. 8, 2006

(54) ***DAHLIA* PLANT NAMED 'KARMA PROSPERO'**

(50) Latin Name: *Dahlia hybrida*
Varietal Denomination: Karma Prospero

(75) Inventor: Aad W. M. Verwer, Lisse (NL)

(73) Assignee: Verwer Dahlias B.V., Lisse (NL)

( * ) Notice: Subject to any disclaimer, the term of this patent is extended or adjusted under 35 U.S.C. 154(b) by 0 days.

(21) Appl. No.: 11/118,993

(22) Filed: Apr. 30, 2005

(51) Int. Cl.
*A01H 5/00* (2006.01)

(52) U.S. Cl. ..... Plt./321
(58) Field of Classification Search ..... Plt./321
See application file for complete search history.

*Primary Examiner*—Kent Bell
(74) *Attorney, Agent, or Firm*—C. A. Whealy

(57) ABSTRACT

A distinct cultivar of *Dahlia* plant named 'Karma Prospero', characterized by its straight and strong flowering stems; freely basal branching growth habit; decorative-type inflorescence form; light red purple-colored ray florets; excellent garden performance; and excellent inflorescence longevity.

2 Drawing Sheets

Botanical designation: *Dahlia hybrida.*
Cultivar denomination: 'Karma Prospero'.

BACKGROUND OF THE INVENTION

The present Invention relates to a new and distinct cultivar of *Dahlia* plant, botanically known as *Dahlia hybrida* and hereinafter referred to by the name 'Karma Prospero'.

The new *Dahlia* is a product of a planned breeding program conducted by the Inventor in Lisse, The Netherlands. The objective of the breeding program is to create new cut flower *Dahlia* cultivars with straight strong flowering stems, decorative inflorescence form, attractive ray floret colors, and good inflorescence longevity.

The new *Dahlia* originated from a cross-pollination made by the Inventor in summer of 2000 of the *Dahlia hybrida* cultivar Silver Years, not patented, as the female or seed parent with an unknown selection of *Dahlia hybrida* as the male or pollen parent. The new *Dahlia* was discovered and selected by the Inventor as a single flowering plant within the progeny of the stated cross-pollination grown in a controlled environment in Lisse, The Netherlands, during the summer of 2001. The selection of this plant was based on its strong straight stems and attractive ray floret coloration.

Asexual reproduction of the new *Dahlia* by cuttings was first conducted in a controlled environment in Lisse, The Netherlands during the spring of 2002. Asexual reproduction by cuttings has shown that the unique features of this new *Dahlia* are stable and reproduced true to type in successive generations.

SUMMARY OF THE INVENTION

The cultivar Karma Prospero has not been observed under all possible environmental conditions. The phenotype may vary somewhat with variations in environment such as temperature, daylength and light intensity without, however, any variance in genotype.

The following traits have been repeatedly observed and are determined to be the unique characteristics of 'Karma Prospero'. These characteristics in combination distinguish 'Karma Prospero' as a new and distinct *Dahlia* cultivar:

1. Straight and strong flowering stems.
2. Freely basal branching growth habit.
3. Decorative-type inflorescence form.
4. Light red purple-colored ray florets.
5. Excellent garden performance.
6. Excellent inflorescence longevity.

Plants of the new *Dahlia* can be compared to plants of the female parent, the cultivar Silver Years, However, in side-by-side comparisons conducted in Lisse, The Netherlands, plants of the new *Dahlia* differed from plants of the cultivar Silver Years in the following characteristics:

1. Plants of the new *Dahlia* had straighter flowering stems than plants of the cultivar Silver Years.
2. Plants of the new *Dahlia* had larger inflorescences than plants of the cultivar Silver Years.
3. Ray florets of plants of the new *Dahlia* were light red purple in color whereas ray florets of plants of the cultivar Silver Years were pale pink in color.

Plants of the new *Dahlia* can also be compared to plants of the cultivar Karma Ventura, disclosed in U.S. Plant Pat. No. 14,602. However, in side-by-side comparisons conducted in Lisse, The Netherlands, plants of the new *Dahlia* differed from plants of the cultivar Karma Ventura in the following characteristics:

1. Plants of the new *Dahlia* were more open than plants of the cultivar Karma Ventura.
2. Plants of the new *Dahlia* had darker green-colored leaves than plants of the cultivar Karma Ventura.
3. Plants of the new *Dahlia* flowered earlier than plants of the cultivar Karma Ventura.
4. Plants of the new *Dahlia* had larger inflorescences than plants of the cultivar Karma Ventura.
5. Plants of the new *Dahlia* and the cultivar Karma Ventura differed in ray floret coloration.

BRIEF DESCRIPTION OF THE PHOTOGRAPHS

The accompanying colored photographs illustrate the overall appearance of the new *Dahlia* showing the colors as true as it is reasonably possible to obtain in colored reproductions of this type. Colors in the photographs may differ from the color values cited in the detailed botanical description which accurately describe the colors of the new *Dahlia.*

The photograph on the first sheet comprises a side perspective view of typical flowering stems of 'Karma Prospero'.

The photograph on the second sheet is a close-up view of a typical inflorescence of 'Karma Prospero'.

DETAILED BOTANICAL DESCRIPTION

In the following description, color references are made to The Royal Horticultural Society Colour Chart, 1995 Edition, except where general terms of ordinary dictionary significance are used. The aforementioned photographs and the following observations and measurements describe plants grown and flowered during the summer and early autumn in Lisse, The Netherlands, in an outdoor nursery and under conditions which approximate those generally used in commercial production. During the production of the plants, day temperatures ranged between 15 and 30° C. and night temperatures ranged between 10 and 20° C. Plants were pinched one time about three to four weeks after planting rooted cuttings. Plants were about four months old when the photographs and the description were taken.

Botanical classification: *Dahlia hybrida* cultivar Karma Prospero.

Parentage:

*Female, or seed, parent.*—*Dahlia hybrida* cultivar Silver Years, not patented.

*Male, or pollen, parent.*—Unknown selection of *Dahlia hybrida,* not patented.

Propagation:

*Type.*—By vegetative cuttings.

*Time to initiate roots.*—Summer: About 10 days at 18° C. Winter: About 13 days at 18° C.

*Time to produce a rooted young plant.*—Summer: About 23 days at 18° C. Winter: About 26 days at 18 to 20° C.

*Root description.*—Fine, fibrous and well-branched; older roots, fleshy.

*Tuber description.*—Shape: Fusiform. Clump diameter: About 25 cm. Color: Close to 199C.

Plant description:

*Appearance.*—Perennial decorative-type inflorescence cut flower *Dahlia.* Straight and strong flowering stems; inverted triangle; moderately vigorous growth habit.

*Plant height.*—About 110 cm.

*Plant diameter.*—About 40 cm.

*Flowering stem description.*—Quantity of flowering stems per plant: Plants produce about eight flowering stems. Length: About 90 cm. Diameter: About 5 mm. Internode length: About 17 cm. Strength: Strong. Aspect: Erect, straight. Texture: Glabrous, smooth. Color: 187A.

*Foliage description.*—Arrangement: Leaves opposite; leaves may be simple or compound with three or five leaflets. Shape: Ovate. Apex: Acuminate. Base: Attenuate. Margin: Serrate. Length: Simple leaves: About 7 cm. Compound leaves with three leaflets: About 20 cm. Compound leaves with five leaflets: About 14 cm. Width: Single leaves: About 7 cm. Compound leaves with three leaflets: About 13 cm. Compound leaves with five leaflets: About 14 cm. Venation pattern: Pinnate. Texture: Smooth, glabrous; leathery. Color: Developing foliage, upper surface: 137C. Developing foliage, lower surface: 191A. Fully developed foliage, upper surface: 137A. Fully developed foliage, lower surface: 191A. Venation, upper surface: 187A. Venation, lower surface: 137C. Petioles: Length: About 9 cm. Diameter: About 4 mm. Texture, upper and lower surfaces: Smooth, glabrous. Color, upper surface: 187B. Color, lower surface: 153A.

Inflorescence description:

*Appearance.*—Decorative-type inflorescence form. Inflorescences borne on terminals, arising from leaf axils. Ray and disc florets develop acropetally on the receptacle. Inflorescences not fragrant. Inflorescences persistent.

*Flowering response.*—Flowering recurrent to continuous during the summer and autumn in The Netherlands. Plants start flowering about 70 days after planting.

*Postproduction longevity.*—On the plant, inflorescences maintain good color and substance for about 25 days in an outdoor environment. As cut flowers, inflorescences maintain good color and substance for about ten days in an indoor environment.

*Quantity of inflorescences per flowering stem.*—One per lateral stem; about 24 to 30 inflorescences per plant develop during the growing season.

*Inflorescence size.*—Shape, in profile: Roughly hemispherical. Diameter: About 15 cm. Depth (height): About 7 cm. Diameter of disc: About 2 cm; inconspicuous. Receptacle diameter: About 2.2 cm. Receptacle height: About 6 mm.

*Inflorescence buds* (*just before opening*).—Length: About 1.6 cm. Diameter: About 2.2 cm. Shape: Oblate. Color: Mid-section and towards the apex, 151A; towards the base, 144A.

*Ray florets.*—Length, fully developed: About 5.6 cm. Width, fully developed: About 2.1 cm. Shape: Ovate. Apex: Acute. Base: Fused. Margin: Entire. Texture: Smooth, glabrous; satiny. Number of ray florets per inflorescence: About 176 arranged in about 22 rows. Venation pattern: Parallel. Color: When opening, upper surface: 65A; towards the base, 155A; longitudinal ridges, 74B. When opening, lower surface: 73A; towards the base, 155A; longitudinal ridges, 74A. Fully opened, upper surface: 65A; towards the base, 155A; longitudinal ridges, 74C; with development, color becomes closer to 69B along the margins. Fully opened, lower surface: 75C; towards the base, 155B; longitudinal ridges, 74B.

*Disc florets.*—Number of disc florets per inflorescence: About 22. Shape: Tubular, elongated. Apex: Five-pointed. Base: Fused. Length: About 1.9 cm. Diameter, apex: About 2 mm. Diameter, base: About 1.5 mm. Color: Immature: 2B. Mature: Apex: 14A. Mid-section: 14B. Base: 1B.

*Phyllaries.*—Quantity: One whorl with about seven phyllaries. Shape: Ovate. Apex: Acute. Base: Attenuate. Margin: Entire. Length: About 2.2 cm. Width: About 1.2 cm. Texture, upper and lower surfaces: Smooth, glabrous. Color, upper surface: 146B. Color, lower surface: 146A blushed with 187A.

*Peduncles.*—Length, terminal peduncle: About 80 cm. Length, fourth peduncle: About 35 cm. Length, seventh peduncle: About 20 cm. Diameter: About 2.2 cm. Strength: Strong. Texture: Smooth, glabrous. Color: 187A.

*Reproductive organs.*—Androecium: Present on disc florets only. Stamen quantity: About five per floret. Anther length: About 4.5 mm. Anther shape: Linear. Anther color: 21B. Pollen amount: Scarce. Pollen color: 17B. Gynoecium: Present on ray and disc florets. Pistil quantity: One per floret. Pistil length: About 3.2 mm. Stigma shape: Lanceolate. Stigma color: 25A. Style length: About 8 mm. Style color: 150D. Ovary color: 2D.

*Seed.*—Length: About 8 mm. Diameter: About 1.5 mm. Color: 200A.

Disease/pest resistance: Resistance to pathogens and pests common to *Dahlias* has not been observed on plants grown under commercial greenhouse or outdoor conditions.

Weather tolerance: Plants of the new *Dahlia* have been observed to be very tolerant to wind, rain and full sun conditions. Plants of the new *Dahlia* have been observed to tolerate temperatures from 0 to 40° C.

It is claimed:

1. A new and distinct cultivar of *Dahlia* plant named 'Karma Prospero', as illustrated and described.

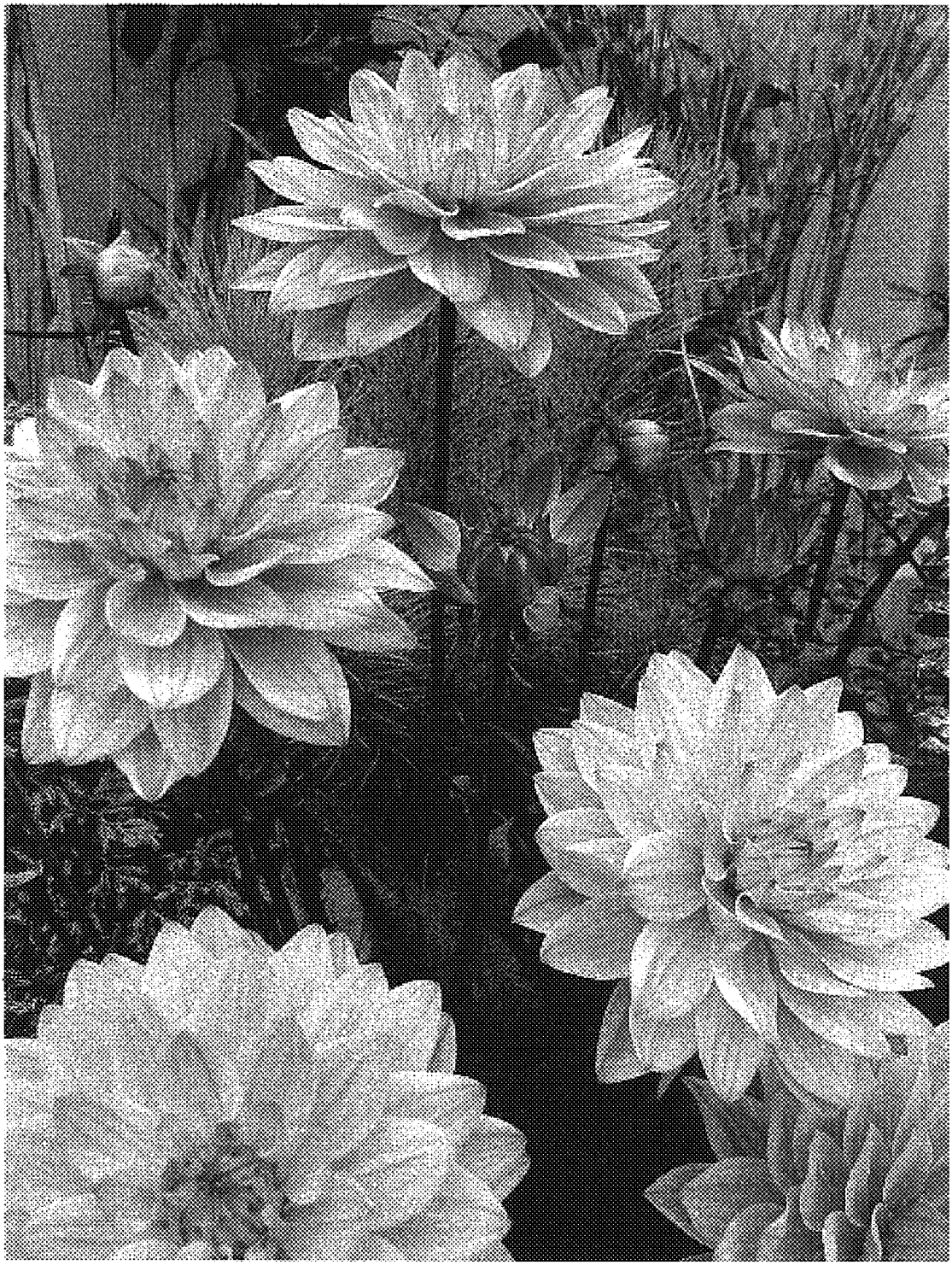

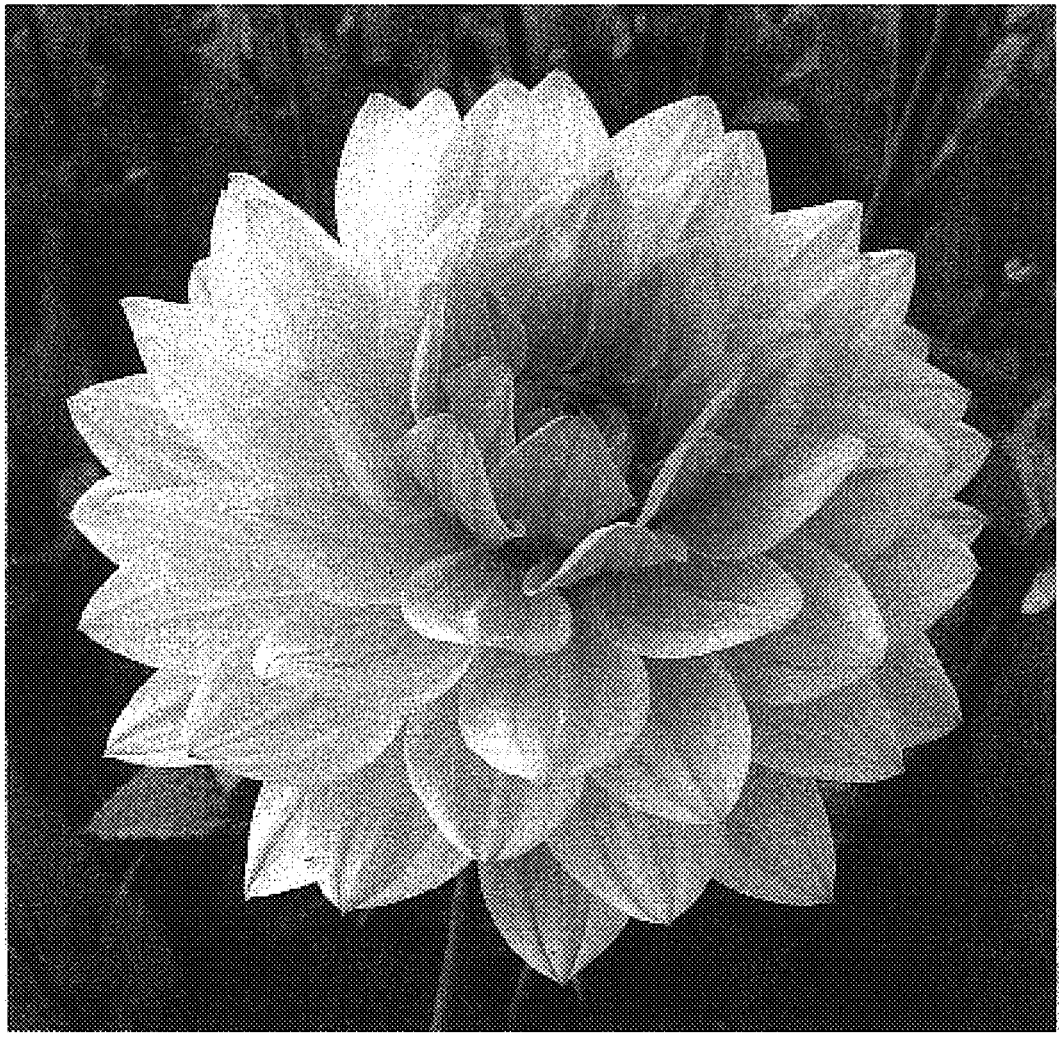

* * * * *